US00PP14689P29

(12) United States Plant Patent
Goetz

(10) Patent No.: US PP14,689 P2
(45) Date of Patent: Apr. 13, 2004

(54) FUCHSIA PLANT NAMED 'GOETZCARL'

(50) Latin Name: *Fuchsia×hybrida*
Varietal Denomination: Goetzcarl

(76) Inventor: Wolfram Goetz, Brahmsweg 3, D-89542 Hebrechtingen (DE)

( * ) Notice: Subject to any disclaimer, the term of this patent is extended or adjusted under 35 U.S.C. 154(b) by 0 days.

(21) Appl. No.: 10/385,252

(22) Filed: Mar. 10, 2003

(51) Int. Cl.[7] ..... A01H 5/00
(52) U.S. Cl. ..... Plt./300
(58) Field of Search ..... Plt./300

(56) References Cited

U.S. PATENT DOCUMENTS

PP1,201 P * 7/1953 Tiret ..... Plt./300
PP1,202 P * 7/1953 Tiret ..... Plt./300
PP1,309 P * 10/1954 Tiret ..... Plt./300

OTHER PUBLICATIONS

UPOV ROM GTITM Computer Database, GTI Jouve Retrieval Software 2003/04 Citation for 'Goetzcarl'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Fuchsia plant named 'Goetzcarl', characterized by its upright, somewhat outwardly spreading and compact plant habit; freely branching habit; dense and full plant growth habit; and numerous violet and red-colored flowers.

1 Drawing Sheet

Botanical classification/cultivar designation: *Fuchsia×hybrida* cultivar Goetzcarl.

BACKGROUND OF THE INVENTION

The present invention relates to a new and distinct cultivar of Fuchsia plant, botanically known as *Fuchsia×hybrida*, and hereinafter referred to by the name 'Goetzcarl'.

The new Fuchsia is a product of a planned breeding program conducted by the Inventor in Hebrechtingen, Germany. The objective of the breeding program was to create new Fuchsia cultivars with compact plant habit and numerous attractive flowers.

The new Fuchsia originated from a cross-pollination made by the Inventor of a proprietary selection *Fuchsia×hybrida* identified as code number 370/97, not patented, as the female, or seed, parent with a proprietary selection *Fuchsia×hybrida* identified as code number 129/97, not patented, as the male, or pollen, parent. The cultivar Goetzcarl was discovered and selected by the Inventor as a flowering plant within the progeny of the stated cross-pollination in a controlled environment in Hebrechtingen, Germany, during the summer of 1997.

Asexual reproduction of the new Fuchsia by terminal cuttings taken at Hebrechtingen, Germany has shown that the unique features of this new Fuchsia are stable and reproduced true to type in successive generations.

BRIEF SUMMARY OF THE INVENTION

The cultivar Goetzcarl has not been observed under all possible environmental conditions. The phenotype may vary somewhat with variations in environment such as temperature and daylength, without, however, any variance in genotype.

The following traits have been repeatedly observed and are determined to be the unique characteristics of 'Goetzcarl'. These characteristics in combination distinguish 'Goetzcarl' as a new and distinct Fuchsia cultivar:

1. Upright, somewhat outwardly spreading and compact plant habit.
2. Freely branching habit; dense and full plant growth habit.
3. Numerous violet and red-colored flowers.

Sepal color of plants of the new Fuchsia is more intense than sepal color of plants of the female parent. In addition, plants of the new Fuchsia flower earlier than plants of the female parent. Plants of the new Fuchsia are more compact and more freely flowering than plants of the male parent.

Plants of the new Fuchsia can be compared to the cultivar Goetzviol, disclosed in a U.S. Plant Patent application filed concurrently. In side-by-side comparisons conducted in Hebrechtingen, Germany, plants of the new Fuchsia had larger leaves than plants of the cultivar Goetzviol and differed in flower coloration.

BRIEF DESCRIPTION OF THE PHOTOGRAPHS

The accompanying colored photographs illustrate the overall appearance of the new Fuchsia, showing the colors as true as it is reasonably possible to obtain in colored reproductions of this type. Colors in the photographs may differ slightly from the color values cited in the detailed botanical description which more accurately describe the colors of the new Fuchsia.

The photograph at the top of the sheet comprises a side perspective view of three typical flowering plants of 'Goetzcarl' grown in a 15-cm container.

The photograph at the bottom sheet is a close-up view of typical flowers, flower buds and leaves of 'Goetzcarl'.

DETAILED BOTANICAL DESCRIPTION

The aforementioned photographs and following observations and measurements describe plants grown in Bonsall, Calif., under commercial practice during the winter in a polypropylene-covered shadehouse with day temperatures ranging from 18 to 35° C., night temperatures ranging from 7 to 18° C., and light levels about 5,000 to 7,000 foot-candles. Three rooted cuttings were planted per 15-cm container and plants were grown for about nine weeks. In the following description, color references are made to The Royal Horticultural Society Colour Chart, 1995 Edition, except where general terms of ordinary dictionary significance are used.

Botanical classification: *Fuchsia×hybrida* cultivar Goetzcarl.

Parentage:

*Female or seed parent.*—Proprietary selection of *Fuchsia×hybrida* identified as code number 370/97, not patented.

*Male, or pollen, parent.*—Proprietary selection of *Fuchsia×hybrida* identified as code number 129/97, not patented.

Propagation:

*Type cutting.*—Terminal cuttings.

*Time to initiate roots.*—About two to three weeks.

*Time to produce a rooted cutting.*—About eight weeks.

*Root description.*—Fine and freely-branching; white to light brown in color.

Plant description:

*Form.*—Upright, somewhat outwardly spreading and compact plant habit; inverted triangle. Freely branching habit; dense and full plants; about four lateral branches develop per plant; pinching (removal of terminal apex) enhances lateral branch development. Freely flowering. Moderately vigorous.

*Plant height at flowering.*—About 21 cm.

*Plant diameter at flowering.*—About 15 cm.

*Lateral branch description.*—Length: About 15 cm. Diameter: About 3 mm. Internode length: About 3.1 cm. Strength: Strong. Texture: Slightly pubescent. Color: 146B.

*Foliage description.*—Arrangement: Simple, opposite. Length: About 3.3 cm. Width: About 1.8 cm. Shape: Ovate to lanceolate. Apex: Acute. Base: Obtuse. Margin: Mostly entire with a few shallow points. Texture, upper and lower surfaces: Smooth, glabrous. Venation pattern: Pinnate, arcuate. Petiole length: About 1 cm. Petiole diameter: About 1 mm. Petiole texture, upper and lower surfaces: Smooth, glabrous. Color: Developing and fully expanded leaves, upper surface: 147A. Developing and fully expanded leaves, lower surface: 147B. Venation, upper surface: 147B. Venation, lower surface: 147C. Petiole, upper and lower surfaces: 146B.

Flower description:

*Flower type and habit.*—Single bi-colored axillary flowers. Freely flowering; potentially two flowers per leaf axil; about two to three open flowers and about eight flower buds per lateral branch. Flowers not persistent. Flowers not fragrant.

*Natural flowering season.*—March through October in southern California; flowering continuous during this period.

*Flower longevity.*—Flowers last about five days on the plant.

*Flower orientation.*—Initially upright, then pendulous.

*Flower diameter.*—About 4.5 cm.

*Flower height.*—About 5.5 cm.

*Flower buds.*—Shape: Elongated, ovoid. Length: About 2.6 cm. Width: About 8 mm. Color: Towards the apex, 52A; towards the base, 53B.

*Petals.*—Quantity: Four; arranged in a single whorl, imbricate. Length: About 1.5 cm. Width: About 1.7 cm. Shape: Ovate to cordate. Apex: Slightly emarginate. Margin: Entire. Texture, upper and lower surfaces: Glabrous, smooth, velvety. Color: When opening, upper and lower surfaces: Darker than 90A. Fully opened, upper and lower surfaces: 90B; towards the base, 58B; with development, color becoming closer to 77A.

*Sepals.*—Quantity: Four; arranged in a single whorl, fused at base. Length, from apex of tube to apex of sepals: About 2.6 cm. Length, tube: About 8 mm. Width: About 8 mm. Tube diameter: About 5 mm. Shape: Narrowly elliptic to linear. Apex: Acuminate. Margin: Entire. Texture, upper and lower surfaces: Glabrous, smooth. Color: When opening, upper surface: 52A. When opening, lower surface: 53C. Fully opened, upper and lower surfaces: 52A. Tube: 52A.

*Peduncles.*—Length: About 1.2 cm. Diameter: About 1.5 mm. Aspect: Horizontal to arching. Strength: Strong. Texture: Smooth, glabrous. Color: 144A.

*Reproductive organs.*—Stamens: Stamen number: Eight per flower. Anther size: About 2 mm by 2 mm. Anther shape: Nearly round. Anther color: 53B. Pollen amount: Scarce. Pollen color: 10C. Pistils: Pistil number: One per flower. Pistil length: About 5.2 cm. Style length: About 4.6 cm. Style color: 67D. Stigma shape: Rounded, four-segmented. Stigma color: 10D. Ovary color: 144A.

*Seed/fruit.*—Seed and fruit production has not been observed.

Disease/pest resistance: Plants of the new Fuchsia have not been observed to be resistant to pathogens and pests common to Fuchsias.

Temperature tolerance: Plants of the new Fuchsia have been observed to tolerate low temperatures of 0° C. and high temperatures of 38° C.

Garden performance: Plants of the new Fuchsia perform have been observed to perform well in the garden and are tolerant to rain and wind.

It is claimed:

1. A new and distinct cultivar of Fuchsia plant named 'Goetzcarl', as illustrated and described.

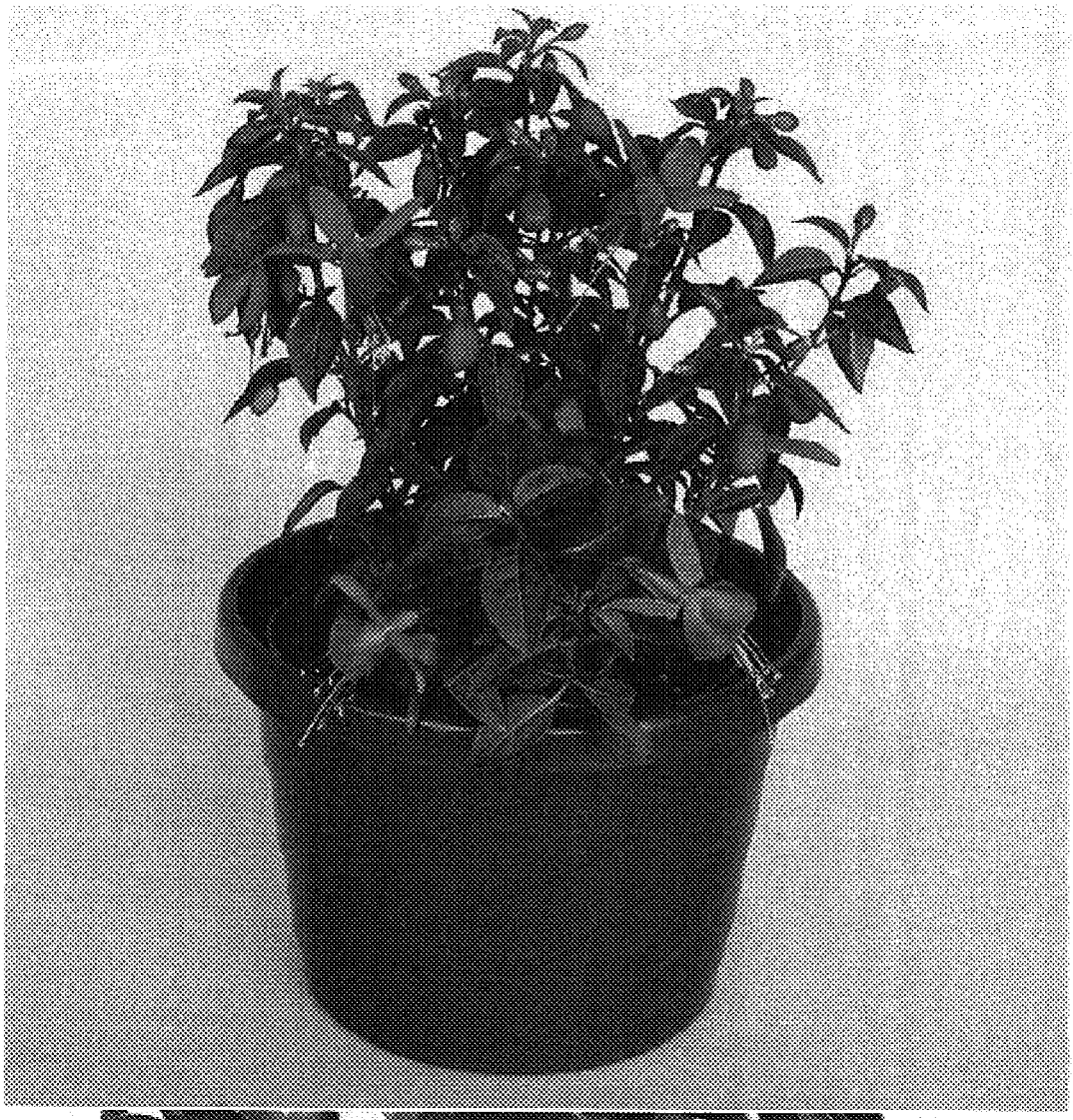
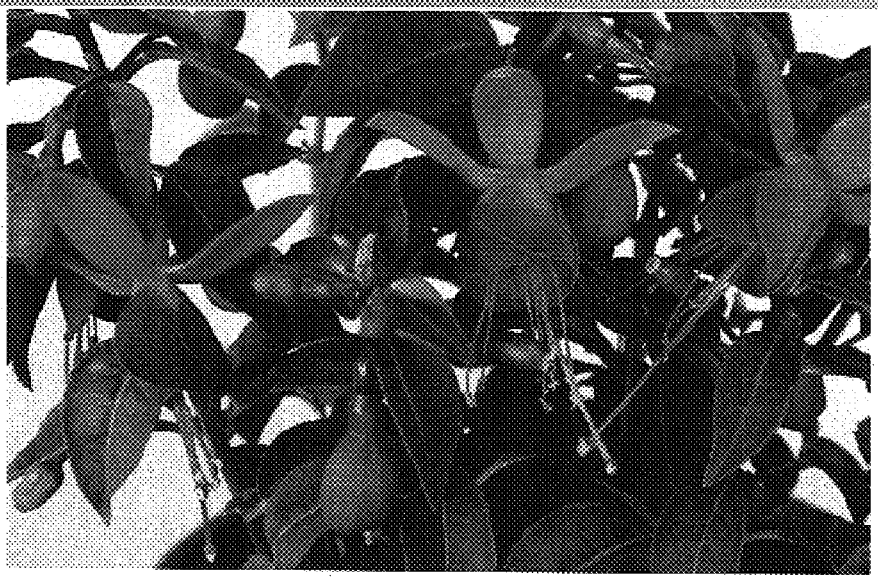

* * * * *